(12) United States Patent
Hunter et al.

(10) Patent No.: US 7,445,663 B1
(45) Date of Patent: Nov. 4, 2008

(54) ENERGY EFFICIENT OXYGEN CONCENTRATOR

(75) Inventors: Donald W. Hunter, Somserset, PA (US); Frank R. Frola, Somerset, PA (US)

(73) Assignee: Sunrise Medical HHG Inc., Longmont, CO (US)

( * ) Notice: Subject to any disclaimer, the term of this patent is extended or adjusted under 35 U.S.C. 154(b) by 389 days.

(21) Appl. No.: 11/249,610

(22) Filed: Oct. 13, 2005

Related U.S. Application Data (60) Provisional application No. 60/620,943, filed on Oct. 21, 2004.

(51) Int. Cl.
*B01D 53/047* (2006.01)

(52) U.S. Cl. ................ 95/96; 95/98; 128/204.21; 128/205.24

(58) Field of Classification Search ......... 95/96, 95/98, 105, 128; 128/204.18, 204.19, 204.21, 128/204.23, 205.12, 205.24
See application file for complete search history.

(56) References Cited

U.S. PATENT DOCUMENTS

| | | | | | |
|---|---|---|---|---|---|
| 3,703,068 | A | * | 11/1972 | Wagner | .......... 95/11 |
| 4,323,370 | A | * | 4/1982 | Leitgeb | .......... 95/23 |
| 4,927,434 | A | | 5/1990 | Cordes et al. | .......... 55/20 |
| 5,042,994 | A | * | 8/1991 | Smolarek | .......... 95/1 |
| 5,256,174 | A | * | 10/1993 | Kai et al. | .......... 96/116 |
| 5,258,056 | A | * | 11/1993 | Shirley et al. | .......... 95/22 |
| 5,340,381 | A | * | 8/1994 | Vorih | .......... 95/21 |
| 5,407,465 | A | * | 4/1995 | Schaub et al. | .......... 95/14 |
| 5,529,611 | A | * | 6/1996 | Monereau et al. | .......... 95/101 |
| 5,871,564 | A | | 2/1999 | McCombs | .......... 95/98 |
| 5,989,313 | A | * | 11/1999 | Mize | .......... 95/10 |
| 6,068,680 | A | * | 5/2000 | Kulish et al. | .......... 95/98 |
| 6,090,185 | A | * | 7/2000 | Monereau et al. | .......... 95/102 |
| 6,348,082 | B1 | * | 2/2002 | Murdoch et al. | .......... 95/22 |
| 6,383,256 | B1 | * | 5/2002 | Phillips | .......... 95/12 |

* cited by examiner

*Primary Examiner*—Frank M Lawrence
(74) *Attorney, Agent, or Firm*—MacMillan, Sobanski & Todd, LLC (57) ABSTRACT

An energy efficient oxygen concentrator in which a compressor applies pressurized air to at least two gas separating elements which will pass a flow of oxygen while blocking a flow of nitrogen. The gas separating elements are alternately cycled between a gas separating mode for producing oxygen enriched gas and a purge mode for purging nitrogen from the elements. According to the invention, the speed of the cycle time is increased as the oxygen enriched gas flow requirement is decreased below the maximum concentrator output. The higher cycle speed reduces the maximum compressor pressure to reduce energy consumption.

5 Claims, 6 Drawing Sheets

ENERGY EFFICIENT OXYGEN CONCENTRATOR

CROSS-REFERENCE TO RELATED APPLICATIONS

Applicants claim priority to U.S. Provisional Patent Application Ser. No. 60/620,943 filed Oct. 21, 2004.

STATEMENT REGARDING FEDERALLY SPONSORED RESEARCH OR DEVELOPMENT

Not Applicable.

TECHNICAL FIELD

The invention relates to an improved efficiency medical oxygen concentrator.

BACKGROUND OF THE INVENTION

Pressure swing oxygen concentrators are frequently used to produce oxygen for medical purposes. A typical pressure swing oxygen concentrator has at least 2 molecular sieve beds which alternately operate to separate nitrogen from air, producing an oxygen enriched gas suitable for medical use. A compressor is connected through a valve to supply a flow of pressurized air to the operating molecular sieve bed which functions as a filter by passing a flow of oxygen and blocking the flow of nitrogen. With time, the operating sieve bed becomes clogged with the separated nitrogen. As the sieve bed becomes clogged, the pressure drop across the sieve bed increases. The increased pressure is necessary to maintain the maximum flow of oxygen enriched gas to maintain the maximum efficiency in gas production. If a sieve bed is operated too long, it will become saturated with and will pass nitrogen, reducing the oxygen concentration of the product gas.

Once the operating sieve bed becomes saturated with nitrogen, valves are operated to connect a different sieve bed to the compressor for producing a flow of oxygen enriched gas and the saturated sieve bed is switched to a purge mode. In the purge mode, the inlet to the sieve bed is vented to atmosphere. The outlet sides of the sieve beds are connected together through a flow restricting orifice which allows a limited flow of pressurized oxygen enriched product gas to flow to the outlet end of the sieve bed in the purge mode to flush nitrogen from the saturated sieve bed. After nitrogen is purged from the sieve bed, the vented inlet side may be closed to allow the pressure to equalize between the sieve beds before the purged bed is switched to the separation mode.

When an oxygen concentrator is operated to produce a maximum flow of oxygen enriched gas, it is not energy efficient. The sieve beds are switched between the separation mode and the purge mode only when necessary. As the separation cycle progresses in a sieve bed, the pressure drop across the sieve bed increases, simultaneously increasing the load on the compressor and the energy required to drive the compressor. However, most patients who require medical oxygen do not require the maximum output flow from the concentrator. For example, an oxygen concentrator may have a 5 liters per minute flow rate, and the patient may only need 2 or 3 liters per minute of supplemental oxygen. An oxygen concentrator operating on a fixed cycle time will require the same energy input for the lower patient flow requirement as for the maximum flow rate, since the compressor produces the same maximum pressure regardless of the oxygen enriched gas flow needed by the patient. The compressor is the most significant energy user in an oxygen concentrator.

The prior art has suggested using a variable speed motor in the compressor in order to reduce the energy required to operated the compressor. However, this requires either a D.C. motor or a variable frequency control, both of which are costly. By slowing down the compressor without changing the cycle time, the sieve bed will have a lower maximum pressure in each cycle. However, if the compressor speed is reduced too much, the oxygen concentration in the product gas also will be reduced.

U.S. Pat. No. 4,272,265 teaches the use of a rotary valve driven by a constant speed motor for controlling the molecular sieve bed cycle in an oxygen concentrator. However, this patent is not concerned with the energy efficiency of the concentrator compressor.

BRIEF SUMMARY OF THE INVENTION

The invention is directed to an oxygen concentrator and to a method for controlling an oxygen concentrator to increase its energy efficiency when a patient's supplemental oxygen requirements are less than the maximum output from the oxygen concentrator. According to the invention, the molecular sieve bed cycle time is shortened as the oxygen requirements decrease. Thus, for lower oxygen flow requirements, each sieve bed is operated in its gas separation mode for a shortened time which does not allow the sieve bed to reach the higher inlet pressure which occurs towards the end of the operating cycle when the cycle time is fixed. By reducing the maximum sieve bed pressure, the maximum compressor load is reduced to reduce energy consumed by the oxygen concentrator.

According to a second feature of the invention, the control method is conveniently implemented in an oxygen concentrator having a rotary valve for switching the molecular sieve beds between the gas separation mode and the purge mode. A stepper motor is used for rotating the valve. The oxygen concentrator controller is programmed to operate the rotary valve to produce the desired oxygen enriched product gas flow for the patient.

Various objects and advantages of the invention will become apparent from the following detailed description of the invention and the accompanying drawings.

DETAILED DESCRIPTION OF THE INVENTION

According to the invention, the cycle time in switching the molecular sieve beds or other gas separation elements is controlled to provide for minimum energy usage based on the patient's oxygen flow rate requirements. As the oxygen enriched gas flow rate requirements decrease, the sieve beds are cycled at a faster rate. As a consequence of operating each sieve bed for a shorter time to produce oxygen enriched gas, the sieve bed is operated at a lower peak pressure than required for optimal gas production. The lower peak pressure across the sieve bed lowers both the concentrated gas flow rate and the energy required to drive the compressor. The oxygen concentrator may be provided with a sensor which measures the instantaneous flow rate of the oxygen enriched gas output. A cycle rate controller which controls valves to switch the molecular sieve beds between the gas separation mode and the purge mode is programmed to respond to the measured output gas flow rate and a programmed rate based on the patient's needs for adjusting the cycle timing.

In the following description, the oxygen concentrator is described as having two molecular sieve beds which are alternately cycled between a gas separation mode and a purge mode. However, it will be appreciated that the invention is not limited to an oxygen concentrator having only two gas separating elements. It is well known in the art that an oxygen concentrators and other types of pressure swing gas separators may have three or more gas separating elements which are rotated between a gas separating mode and a purge mode. The invention also may be applied to these gas separators.

Figure 1:
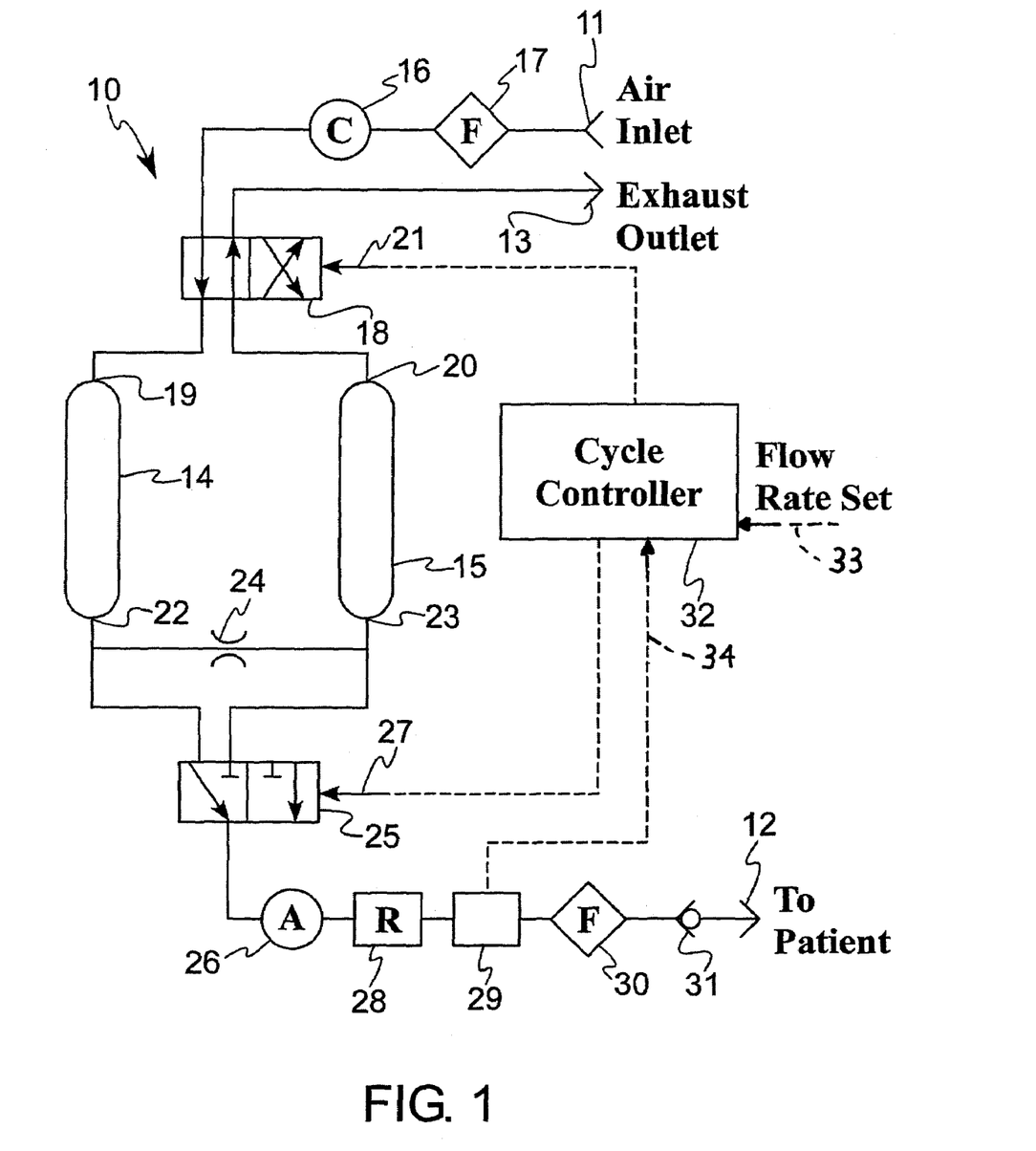
FIG. 1 is a schematic diagram illustrating the pneumatic circuit of an exemplary oxygen concentrator which is operated in accordance to one aspect of the invention.

FIG. 1 is a schematic diagram of an exemplary pressure swing oxygen concentrator 10 incorporating the invention. The oxygen concentrator 10 has an air inlet 11, a pressurized gas outlet 12 for delivering oxygen enriched gas to a patient, and an exhaust gas outlet 13. A gas consisting primarily of nitrogen is separated from air, leaving an oxygen rich product gas. The air is separated in two or more molecular sieve beds 14 and 15, or other known gas separation elements. Each molecular sieve bed is partially filled with a suitable filter material, such as a zeolite, which will allow oxygen molecules while blocking a flow of larger nitrogen molecules. A compressor 16 draws ambient air through a filter 17 and delivers pressurized air through a two position valve 18 alternately to the two molecular sieve beds 14 and 15. The valve 18 has two positions. In the illustrated released position, the valve 18 delivers pressurized air from the compressor 16 to an inlet port 19 on the molecular sieve bed 14, and also connects an inlet port 20 on the molecular sieve bed 15 to the exhaust gas outlet 13 for venting the inlet side of the bed 15 to atmosphere. When the valve 18 is actuated by applying power to a solenoid 21, pressurized air from the compressor 16 is delivered to the inlet port 20 on the molecular sieve bed 15 and the inlet port 19 on the molecular sieve bed 14 is connected to the exhaust outlet 13 for venting the inlet side of the bed 14 to atmosphere.

The molecular sieve beds 14 and 15 have outlet ports 22 and 23, respectively. The outlet ports 22 and 23 are connected together through a calibrated flow restricting orifice 24 to permit a controlled flow of oxygen enriched gas to flow from the highest pressure molecular sieve bed to the lowest pressure molecular sieve bed. A two position solenoid operated valve 25 selectively connects one of the outlet ports 22 or 23 to an oxygen enriched gas accumulator 26. When a solenoid 27 is unactuated as shown in FIG. 1, the valve 25 is connects the outlet port 22 on the sieve bed 22 to the accumulator 26, and when the solenoid 27 is actuated, the outlet port 23 of the sieve bed 15 is connected to the accumulator 26. From the accumulator 26, the oxygen enriched gas flows through a pressure regulator 28, a flow sensor/flow meter 29, a filter 30 and a check valve 31 to the gas outlet 12. The gas outlet 12 is normally connected to a patient via a hose and a nasal cannula (not shown).

In operation, the valves 18 and 25 are operated together and may initially be positioned as illustrated, with the pressurized air from the compressor applied to the inlet port 19 of the molecular sieve bed 14 and the outlet 22 of the molecular sieve bed 14 connected to deliver oxygen enriched gas to the patient. The inlet post 20 on the molecular sieve bed 15 is vented to atmosphere through the valve 18 and the exhaust outlet 13. This causes the molecular sieve bed 15 to have a lower pressure than the molecular sieve bed 14, and controlled amount of oxygen enriched, nitrogen free, gas will flow through the orifice 24 through the outlet port 23 to back flush nitrogen from the molecular sieve bed 15. According to the prior art, after a fixed time interval sufficient for the molecular sieve bed 14 to become saturated and to have a high pressure drop across the sieve bed, the solenoids 21 and 27 on the valves 18 and 27 are both actuated. This switches operation of the molecular sieve beds 14 and 15, so that the inlet port 19 of the bed 14 is vented to atmosphere through the outlet 13, pressurized air is applied from the compressor 16 to the inlet port 20 of the bed 15, and oxygen enriched gas at the outlet port 23 is delivered to the patient and is applied to the outlet port 22 to back flush the molecular sieve bed 14.

According to the invention, the energy efficiency of the oxygen concentrator 10 in improved by providing a programmable cycle controller 32 which controls the timing of the cycle in which the solenoids 21 and 25 operate the valves 18 and 25, respectively. The cycle controller 32 has a flow rate input 33 for setting a desired flow rate for the oxygen enriched gas delivered to the gas outlet 12. The input 33 which may be a manually operated control or the flow rate may be programmed into the controller 32 using known control technology. The controller 32 also has an input 34 from the flow sensor 29 which provides information on the actual flow rate of gas delivered to the patient. The controller 32 controls the operating cycle time of the solenoids 18 and 27. As the set oxygen enriched gas flow rate is decreased from the maximum flow which the concentrator 10 can produce, the cycle time is decreased so that the molecular sieve beds are more rapidly switched between the gas separation and purge modes. This in turn decreases the maximum output pressure from the compressor 16 to decrease its energy consumption.

Another type of prior art oxygen concentrator (not shown) has solenoid operated valves for selective connecting the inlet side of each molecular sieve bed to the output of an air compressor and for selectively venting the inlet side of each sieve bed to atmosphere. When the concentrator has two molecular sieve beds A and B, the valves have four phases of operation: 1) feed the inlet side of bed A and purge bed B by venting its inlet side; 2) block the inlet sides of both beds for pressure equalization through an orifice which connects the outlet sides of the beds; 3) feed the inlet side of bed B and purge bed A by venting its the inlet side; and 4) block the inlet sides of both beds for pressure equalization. In the prior art, the cycle then repeats at a fixed cycle rate. According to the invention, the cycle rate is increased when the patient's oxygen requirements are less than the maximum concentrator output in order to reduce the power consumed by the compressor in the oxygen concentrator. A disadvantage with this oxygen concentrator and with the oxygen concentrator illustrated in FIG. 1 is that valves continuously consume power while actuated.

According to a second aspect of the invention, a stepper motor driven rotary valve is used to control the feeding of compressed air and the venting of the inlet sides of the molecular sieve beds. The stepper motor is operated only and uses power only when changing between valve modes. The rotary valve will maintain its different settings without maintaining power on the stepper motor. The combination of a rotary valve and a stepper motor in an oxygen concentrator allows control over timing steps that could not be as easily achieved in prior art concentrators. By timing the steps, the process can be optimized around the supporting hardware. That is, maximum output can be achieved at minimum power input. Power required to operate the oxygen concentrator is further reduced by speeding up the process steps to unload the compressor for lower flow rates. This actually wastes air, but results in an inexpensive reduced power capacity that reduces operating costs.

According to a further aspect of the invention, a magnet may be mounted on the valve rotor and a hall effect sensor can be mounted to the valve body to permit accurate sensing of the rotor position. Since the number of steps of the stepper motor can be easily counted, the device can determine if the rotor is not turning freely and make adjustments. Under normal operating conditions, the number of stepper motor steps between each detection of the magnet should be constant. If more steps are needed, then the rotor is either sticking or is stuck in a position. As the stepper motor is slowed down, its torque increases, so one option for freeing a stuck rotor is to slow down the stepper motor and thus increase its torque. A second option that the stepper motor provides is to free up the rotor by reversing the direction of rotation.

Figure 2:
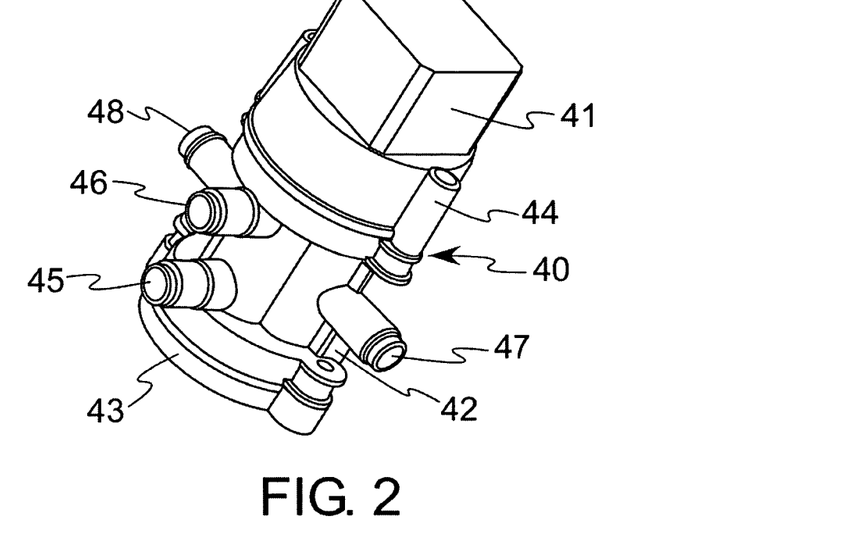
FIG. 2 is a perspective view of a rotary valve according to a second aspect of the invention.
Figure 9:
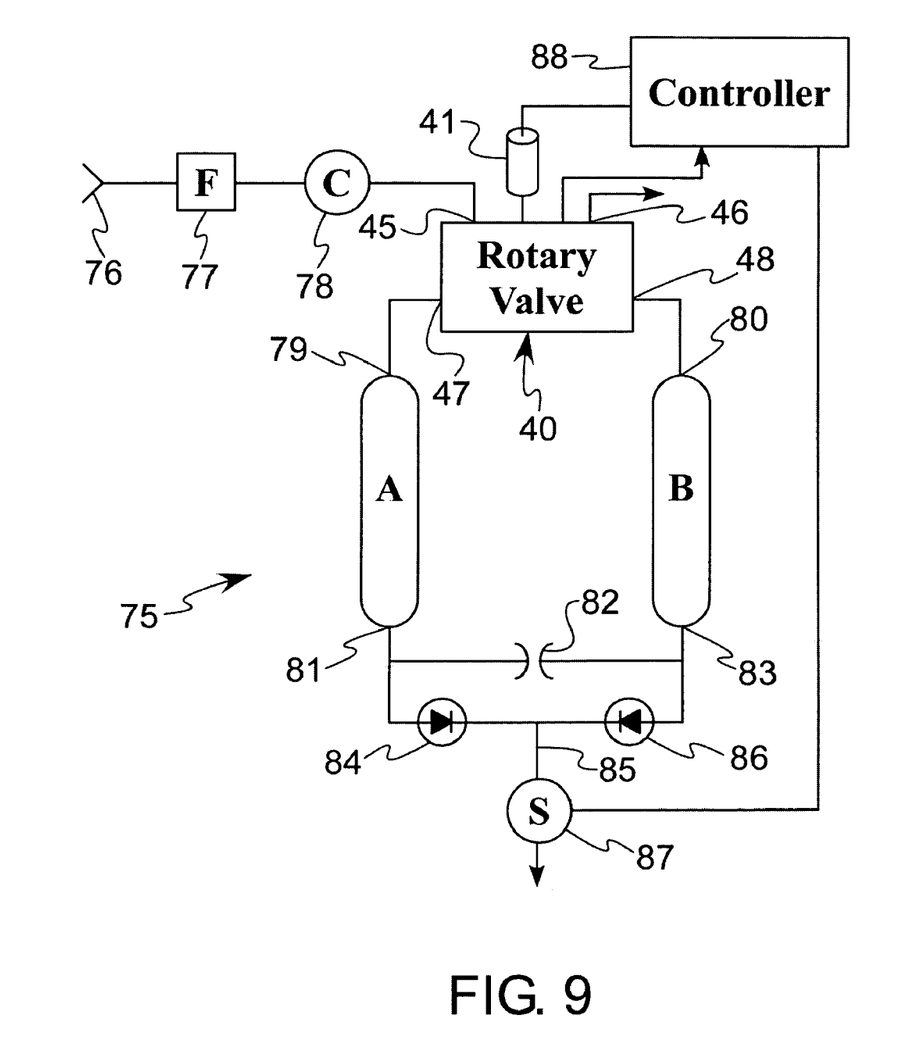
FIG. 9 is a schematic diagram illustrating the pneumatic circuit of an oxygen concentrator circuit incorporating a stepper motor driven rotary valve according to the invention.

FIG. 2 is a perspective view of a rotary valve 40 which is incrementally driven by a stepper motor 41 according to one aspect of the invention. The valve 40 has a body 42 which is closed at one end by a feed cap 43 and at an opposite end by an exhaust cap 44. The body 42 has four ports: a port 45 which is connected to a compressor (not shown), a port 46 which is vented to atmosphere, a port 47 which is connected to the inlet side of a first sieve bed A (FIG. 9), and a port 48 which is connected to the inlet side of a second sieve bed B (FIG. 9).

Figure 3:
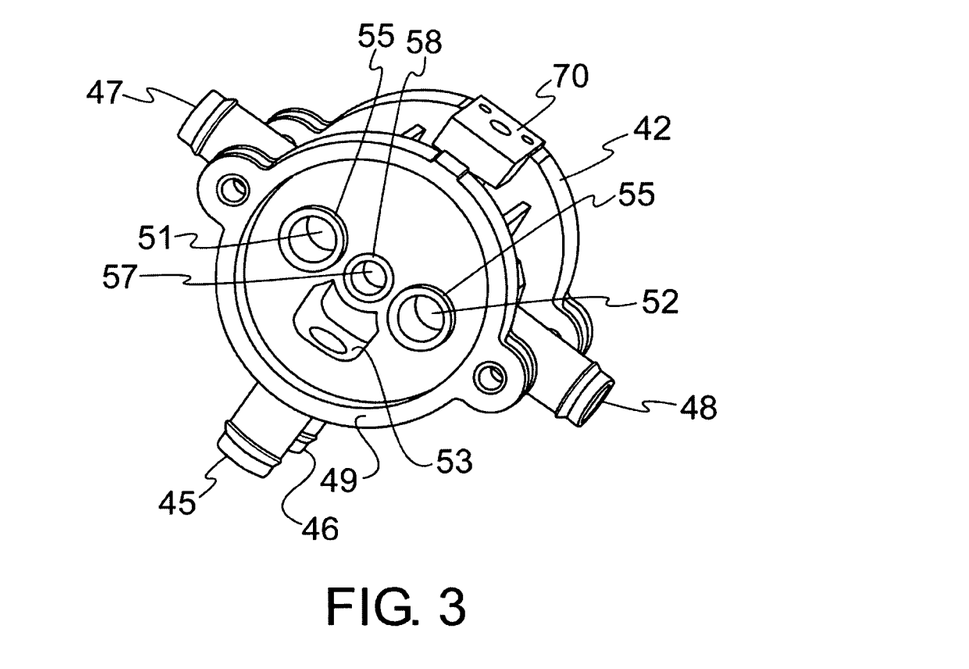
FIG. 3 is a perspective view showing details of the feed cap end of the rotary valve body.
Figure 4:
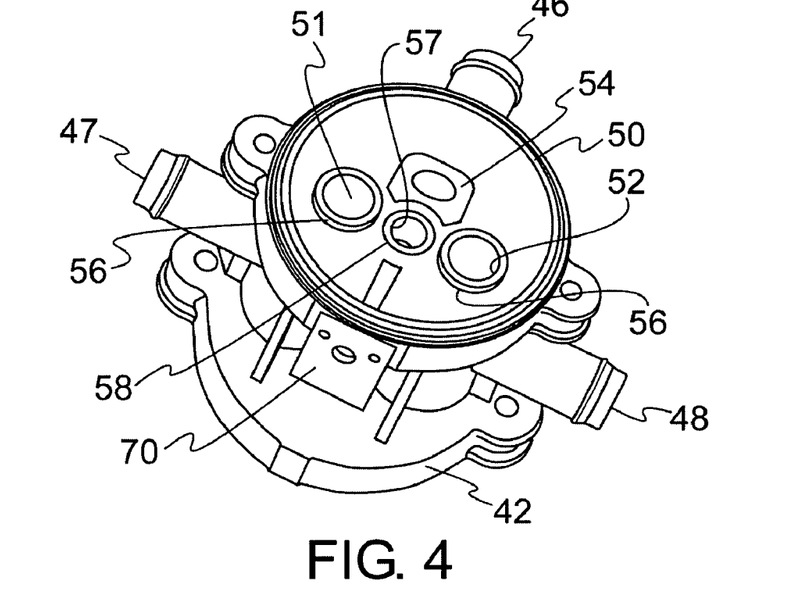
FIG. 4 is a perspective view showing details of the exhaust cap end of the rotary valve body.

FIG. 3 is a perspective view showing details of an end 49 of the body 42 to which the feed cap 43 is mounted and FIG. 4 is a perspective view showing details of an end 50 of the body 42 to which the exhaust cap 44 is mounted. A first passage 51 which extends between the body ends 49 and 50 connects with the port 47 and a passage 52 which extends between the body ends 49 and 50 connects with the port 48. The port 45 connects with a chamber 53 which opens at the body end 49, and the port 46 connects with a chamber 54 which opens at the body end 50. A shoe 55 is positioned in the end of each of the passages 51 and 52 at the feed cap end 49 and a show 56 is positioned in the end of each of the passages 51 and 52 at the exhaust cap end 50. The body 42 also has a central passage 57 extending between the ends 19 and 20. A bushing 58 is located in each end of the passage 27.

Figure 5:
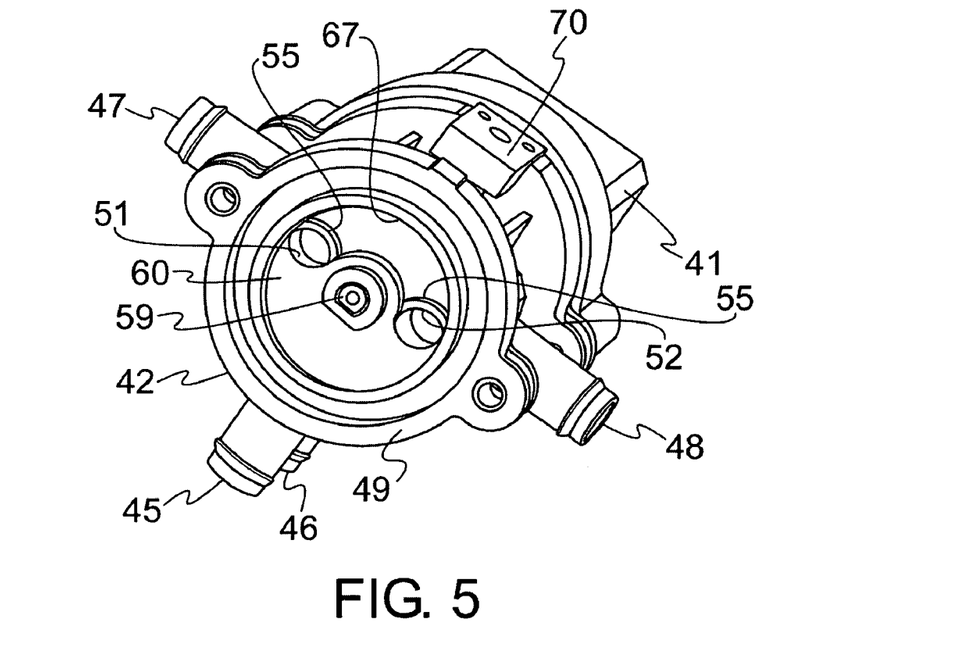
FIG. 5 is a perspective view showing details of the feed gas valve disc and the rotary valve body.
Figure 6:
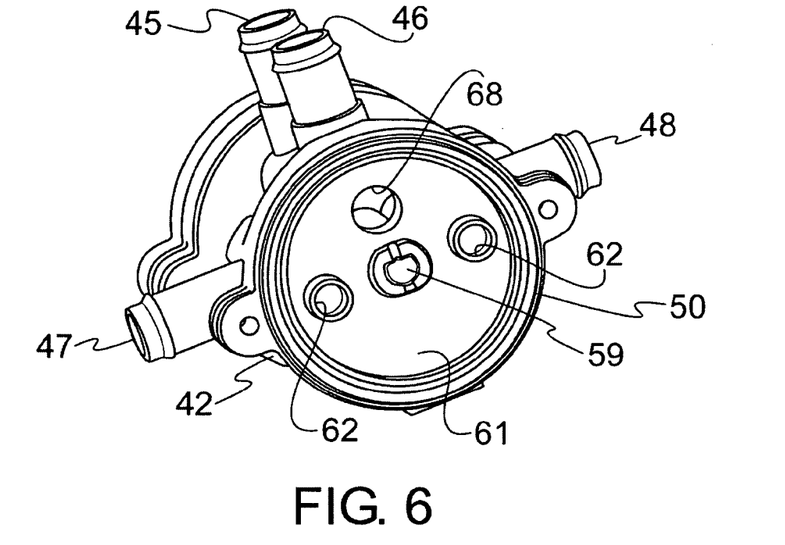
FIG. 6 is a perspective view showing details of the exhaust gas valve disc and the rotary valve body.

A shaft 59 is mounted to extend through the passage 57 to rotate in the bushings 58. As shown in FIGS. 5 and 6, a feed gas valve disc 60 is mounted on the shaft 59 at the feed cap end 49, and an exhaust gas valve disc 61 is mounted on the shaft 59 at the exhaust cap end 50. The discs 60 and 61 are keyed to the shaft 69 so as to rotate together. The shoes 55 seal against the feed gas valve disc 60 while permitting the disc 60 to rotate, and the shoes 56 seal against the exhaust gas valve disc 61 while permitting the disc 61 to rotate.

Figure 7:
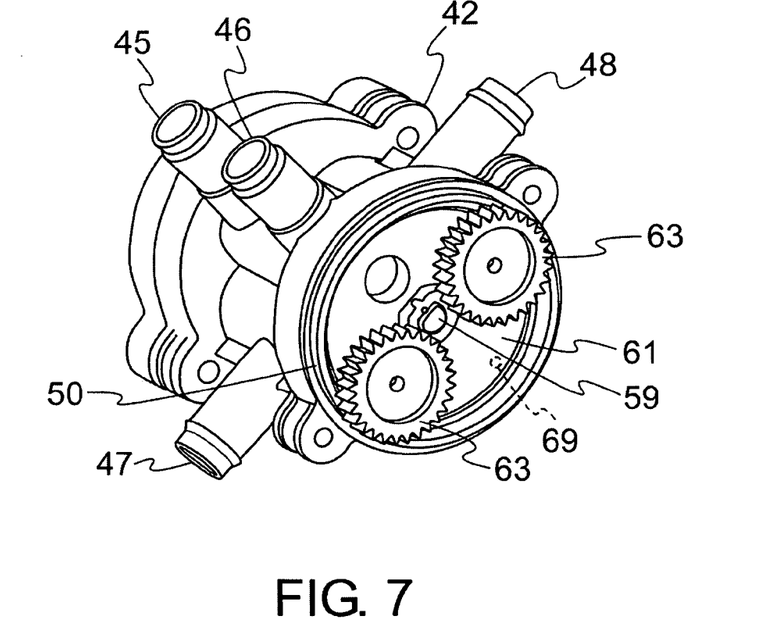
FIG. 7 is a perspective view showing details of the idle gears which are mounted to rotate on the exhaust gas valve disc.
Figure 8:
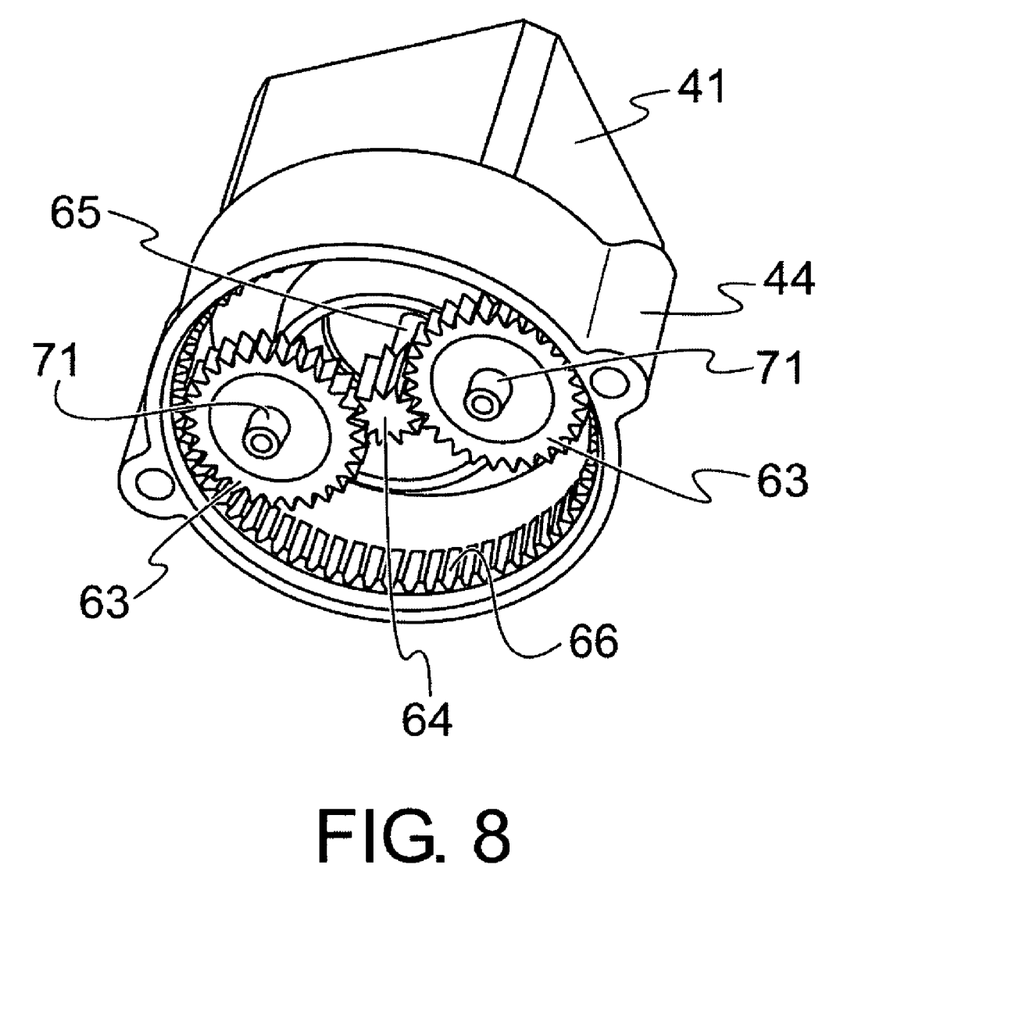
FIG. 8 is a perspective view showing details of the idle gears, the exhaust cap and the stepper motor.

Two sockets 62 are formed on the disc 61 on diametrically opposite sides of the shaft 59. A separate idle gear 63 has a shaft 71 which is positioned to rotate in each socket 62, as shown in FIG. 7. FIG. 8 is a perspective view showing the inside of the exhaust cap 44 with the stepper motor 41 attached to the exhaust cap 44. The stepper motor 41 has a gear 64 on the end of a shaft 65. The gear 34 extends between and engages the isle gears 63. The idle gears 63 also engage a stationary inner ring gear 66 formed on the inside of the exhaust cap 44. As a consequence, when the shaft 65 of the stepper motor 41 is rotated, the idle gears 63 rotate, moving around the exhaust cap 44 to rotate the exhaust gas valve disc 61 which supports the idle gears 63. When the exhaust gas valve disc 61 is rotated, the shaft 59 simultaneously rotates the feed gas valve disc 60.

As shown in FIG. 5, an arcuate slot 67 is formed in the feed gas valve disc 60. The slot 67 is slightly greater than 180° so that each time the feed gas valve disc 30 is rotated through 180°, both of the passages 51 and 52 will be connected together through a chamber defined by the feed gas cap 43. Pressurized feed gas from the compressor flows from the port 45 through the chamber 53 and around the valve disc 60 into the chamber formed by the feed gas cap 43. The pressurized feed gas will then flow into any of the passages 51 and 52 which is aligned with the arcuate slot 67 and thence to the inlet side of a connected molecular sieve bed (not shown).

As shown in FIG. 6, an opening 68 is formed in the exhaust gas valve disc 61. The opening 68 is positioned on the exhaust gas valve disc 61 on the opposite side of the shaft 59 from the arcuate slot 67 on the feed gas valve disc 60. When the opening 68 is aligned with either of the passages 51 and 52, gas from a connected molecular sieve bed will flow through the connected passage 51 or 52 and the exhaust gas valve disc 61 into a chamber formed by the interior of the exhaust cap 44. The gas is then vented around the exhaust gas valve disc 61, through the chamber 54 to the exhaust port 46.

As shown in FIG. 7, a magnet 69 is embedded in the perimeter of the exhaust gas valve disc 61. A Hall effect sensor 70 (FIG. 4) is mounted on the body 42 at a location for detecting when the magnet 69 moves past the sensor 70. Thus, the sensor 70 provides information on the position of the valve discs 60 and 61 and on any failure of the stepper motor 41 to rotate the valve discs 60 and 61. This information may be used to detect if the valve discs should become stuck for driving the stepper motor 1 in a manner to free up the valve discs.

FIG. 9 is a diagrammatic view of an oxygen concentrator 75 incorporating the rotary valve 40. A room air inlet 76 is connected through a filter 77 to a compressor 78. The compressor 78 applies pressurized air to the rotary valve compressor port 45. The exhaust port 46 is vented to atmosphere. An optional noise reducing muffler (not shown) may be connected in series with the exhaust port 46. The valve port 47 is connected to an inlet end 79 of a molecular sieve bed A and the valve port 48 is connected to an inlet end 80 of a molecular sieve bed B. It will be appreciated that the invention also may be implemented with other types of filter elements which will pass a flow oxygen while blocking nitrogen.

An outlet end 81 from the sieve bed A is connected through a flow limiting orifice 82 to an outlet end 83 of the sieve bed B. The outlet end 81 is also connected through a check valve 84 to an oxygen enriched gas outlet 85 and the outlet end 83 is connected through a check valve 86 to the oxygen enriched gas outlet 85. At least one sensor 87 is shown in the outlet 85. The sensor 87 monitors the oxygen concentration in the product gas and also measures the flow rate. Information from the sensor is applied to a controller 58 which controls operation of the rotary valve 40.

The controller 88 includes a microprocessor which can be programmed to control the operation of the rotary valve 40 for maximum energy efficiency. A patient's oxygen flow rate requirement is set into the controller 88. The controller 88 will slow down the valve cycle to produce a higher product gas flow and will speed up the valve cycle to produce a lower flow rate, thus decreasing the energy consumption. As discussed above, a pulse is applied from a sensor in the rotary valve 40 to the controller 88 each time the valve 40 rotates through 360°. If the controller 88 does not receive a pulse from the valve 40, it will initially assume that the rotary valve 40 is stuck. It may then increase the power applied to the stepper motor 41 to increase the torque applied to rotate the valve 40. Alternately, the controller 40 may reverse the direction in which the rotary valve 10 rotates. The valve 40 can be rotated in either direction during operation of the concentrator 85.

It will be appreciated that various modifications and changes may be made to the above described preferred embodiment of without departing from the scope of the following claims. It should be appreciated that the invention may be applied to oxygen concentrators having different types of gas separating elements and having two or more gas separating elements. The invention also is applicable to oxygen concentrators having different arrangements for switching the individual gas separating elements between a gas separating mode and a purge mode.

The invention claimed is:

1. A method for controlling the energy efficiency of a pressure swing oxygen concentrator having a compressor which provides a flow of pressurized feed gas, a plurality of gas separation elements which pass a flow of oxygen while blocking the flow of nitrogen, said oxygen concentrator having an operating cycle in which at least one element separates nitrogen from pressurized feed gas from the compressor to produce oxygen rich gas and in which nitrogen is purged from at least one other gas separation element, and at least one valve for switching the elements between the gas separating mode and the purge mode, said method comprising the steps of:
   a) selecting a desired oxygen enriched gas flow rate from said oxygen concentrator;
   b) providing a rotary valve for switching the elements between the gas separating mode and the purge mode, said rotary valve having a feed gas inlet port, an exhaust port, a first port connected to an inlet side of a first one of the gas separation elements, a second port connected to the inlet side of a second one of the gas separation elements, and a motor controlled by a controller to sequentially move said rotary valve between a first position wherein said inlet port is connected to the first port and said exhaust port is connected to the second port, a second position wherein the inlet port is connected to the first and second ports, a third position wherein the inlet port is connected to the second port and said exhaust port is connected to the first port, and a fourth position wherein the inlet port is connected to the first and second ports; and
   c) controlling the cycle time for the gas separation elements at a rate inverse to the desired oxygen flow rate, whereby as the desired oxygen enriched gas flow rate is decreased below a maximum flow rate for the oxygen concentrator, the gas separation elements are cycled between a gas separation mode and a purge mode at an increased rate by controlling the motor to rotate the rotary valve at a controlled rate.

2. A method for controlling the energy efficiency of a pressure swing oxygen concentrator, as set forth in claim 1, wherein the motor is a stepper motor, and further including the step of incrementally operating said stepper motor to rotate said valve from said first position to said second position, from said second position to said third position, from said third position to said fourth position and from said fourth position back to said first position.

3. A method for controlling the energy efficiency of a pressure swing oxygen concentrator, as set forth in claim 2, and further including the steps of sensing when the stepper motor fails to rotate the rotary valve, and increasing the output torque of the stepper motor in response to sensing when the stepper motor fails to rotate the rotary valve.

4. A method for controlling the energy efficiency of a pressure swing oxygen concentrator, as set forth in claim 2, and further including the steps of sensing when the stepper motor fails to rotate the rotary valve, and reversing the direction of the stepper motor in response to sensing that the stepper motor fails to rotate the rotary valve.

5. A method for controlling the energy efficiency of a pressure swing gas separator which includes an feed gas compressor, first and second gas separating elements which pass a first gas while blocking a flow of a second gas between an inlet port on each element and an outlet port on each element, said method comprising the steps of:
   a) providing a valve having at least a first position in which pressurized feed gas from said compressor is applied to the inlet port of said first element and the inlet port of said second element is vented, a second position in which pressurized feed gas from said compressor is applied to the inlet port of said second element and the inlet port of said first element is vented, and a third position in which pressurized feed gas from said compressor is applied to the inlet port of said first element and the inlet port of said second element, whereby a flow of product gas rich in said first gas is available at an outlet port from the element connected through said valve to said compressor;
   b) alternately cycling said valve between said first position and said second position by rotating said valve; and
   c) controlling the rate of rotation of said valve at a higher speed to increase the cycle rate when a lower product gas flow rate is required and at a lower speed to decrease the cycle rate when a higher product gas flow rate is required, whereby energy consumed by said compressor is reduced as the product gas flow rate decreases.

* * * * *